United States Patent
James et al.

(10) Patent No.: US 10,568,327 B1
(45) Date of Patent: Feb. 25, 2020

(54) METHOD OF CONTROLLING PHYTOPATHOGENIC DISEASES ON TURFGRASS

(71) Applicant: Syngenta Crop Protection LLC, Greensboro, NC (US)

(72) Inventors: John Robert James, Greensboro, NC (US); Michael Agnew, Greensboro, NC (US)

(73) Assignee: Syngenta Participations AG, Basel (CH)

( * ) Notice: Subject to any disclaimer, the term of this patent is extended or adjusted under 35 U.S.C. 154(b) by 407 days.

(21) Appl. No.: 13/861,716

(22) Filed: Apr. 12, 2013

Related U.S. Application Data

(60) Provisional application No. 61/623,553, filed on Apr. 12, 2012.

(51) Int. Cl.
 *A01N 43/82* (2006.01)
 *A01N 37/34* (2006.01)
(52) U.S. Cl.
 CPC .............. *A01N 43/82* (2013.01); *A01N 37/34* (2013.01)
(58) Field of Classification Search
 CPC .................................................... A01N 43/82
 See application file for complete search history.

(56) References Cited

U.S. PATENT DOCUMENTS

| | | | |
|---|---|---|---|
| 5,523,311 A | 6/1996 | Schurter et al. | |
| 2002/0077365 A1 | 6/2002 | Windsor et al. | |
| 2004/0241098 A1* | 12/2004 | Labourdette et al. | 424/40 |
| 2009/0120339 A1 | 5/2009 | Detweiler et al. | |
| 2012/0083497 A1* | 4/2012 | Riggs et al. | 514/239.5 |

FOREIGN PATENT DOCUMENTS

| | | | |
|---|---|---|---|
| WO | 2009/095098 A2 | | 8/2009 |
| WO | WO 2012031061 A2 * | | 9/2011 |
| WO | 2011/153442 A1 | | 12/2011 |
| WO | WO 2012146125 A1 * | | 11/2012 |

OTHER PUBLICATIONS

Allen et al., Pythium blight of turfgrass, The Plant Health Instructor, 2004, available at http://www.apsnet.org/edcenter/intropp/lessons/fungi/Oomycetes/Pages/PythiumBlight.aspx.*
U.S. Appl. No. 13/861,819, filed Apr. 1013, James et al.*
Zhang at al., International Turfgrass Society Research Journal, vol. 10, 2005, 180-185.*
Zhang et al., International Turfgrass Society Research Journal, vol. 10, 2005, 180-185.

* cited by examiner

*Primary Examiner* — Svetlana M Ivanova
(74) *Attorney, Agent, or Firm* — James Cueva

(57) ABSTRACT

The present invention relates to a method of controlling dollar spot on turfgrass, in particular low to moderate disease pressure, using a fungicidally effective non-phytotoxic amount of (A) chlorothalonil and (B) acibenzolar-s-methyl.

12 Claims, No Drawings

METHOD OF CONTROLLING PHYTOPATHOGENIC DISEASES ON TURFGRASS

The present invention relates to a method of controlling phytopathogenic diseases on turfgrass. More specifically, the present invention relates to a method of suppressing or controlling dollar spot on turfgrass with a combination of compounds comprising chlorothalonil and acibenzolar-s-methyl.

There are numerous problems that turfgrass managers face in maintaining turfgrass at a standard of quality expected by users. While the problems are many, those relating to pests (including disease) are particularly challenging to manage and control. Numerous types of pathogens, in particular fungi, infect turfgrass plants on golf courses causing a loss of revenue from reduced playability. One example of a common problem for golf course managers is a dollar spot infection caused by a fungal pathogen (*Sclerotinia homoeocarpa*). Dollar spot blights leaf tissues but typically does not affect turfgrass roots or crowns and results in the formation of small, roughly circular, brown patches in grass growing areas.

Agricultural active chemicals for controlling pathogens, such as fungicides, are typically applied on golf courses as needed depending on the extent of disease pressure, pathogen population, weather, and the like. However, fungicide applications are highly controlled by course budget, availability of appropriate equipment, and availability of qualified personnel for applying the agricultural active chemicals.

One known fungicide management tool useful for control of disease in turfgrass is chlorothalonil (2,4,5,6-tetrachloroisophthalonitrile), which is a polychlorinated aromatic mainly used as a broad spectrum, non-systemic fungicide. Its structure can be represented as:

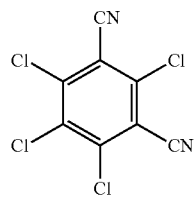 [SMILES: N#Cc1c(Cl)c(Cl)c(Cl)c(C#N)c1Cl]

Chlorothalonil is an economical fungicide with broad-spectrum activity, providing partial to complete control of important turfgrass diseases such as dollar spot, brown patch, leaf spot/melting out, gray leaf spot and others and is considered to be at low risk for resistance due to its multi-site activity. Chlorothalonil is commercially available under the trade name Daconil® (Syngenta Crop Protection, Inc.)

One of the reasons for chlorothalonil usage during turfgrass growing periods is fungicide resistance management. For example, the a.i. can be used in programs with other fungicides that are at higher risk for resistance. Many of the resistance problems on golf courses have occurred due to the dollar spot organism. Chlorothalonil is an important rotational partner in delaying such resistance and, once resistance has occurred, it is one of the most economical way of managing dollar spot.

One challenge occasioned by the use of chlorothalonil for disease control in turfgrass is that the product label sets restrictions and limits on its annual maximum allowable application rate. These restrictions are set by regulatory authorities for environmental and product stewardship reasons. If not managed properly, the maximum allowable rate of chlorothalonil for greens, tees, and fairways can be reached before the end of a growing season. In some instances, it does not take long for the allotted amount of chlorothalonil to be used up. A problem arises when chlorothalonil rate limits are reached before turfgrass disease issues such as dollar spot are completely managed or controlled.

The compound acibenzolar-S-methyl (S-methyl benzo[1,2,3]thiadiazole-7-carbothioate) acts as a functional analogue of the natural signal molecule for systemic activated resistance (SAR), salicylic acid. It activates the host plant's natural defense mechanism. The structure of acibenzolar-S-methyl can be represented as follows:

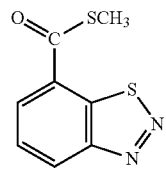 [SMILES: CSC(=O)c1cccc2nnsc12]

Acibenzolar-S-methyl is commercially available under the trade name Actigard® (Syngenta Crop Protection, Inc.).

From Fry et al., Golf Course Management July 2006 it is suggested that the use of certain plant activators such as acibenzolar-S-methyl at rates of 6.1 grams/1,000 square meters may allow for reduction of chlorothalonil rates on creeping bentgrass greens. However, it is reported by Fry that turf quality was below standard at the rates at which acibenzolar-S-methyl was applied.

Zhang et al., International Turfgrass Society Research Journal Volume 10, 2005 discloses an evaluation of plant defense activators including acibenzolar-S-methyl and/or β-aminobutyric acid in conjunction with chlorothalonil applied at a rate lower than currently recommended for dollar spot and brown patch control on creeping bentgrass putting greens. Again, Zhang et al. report turf quality was unacceptable at the rates at which acibenzolar-S-methyl was applied.

High quality, healthy turf is essential, for example, to the golfing industry. Accordingly, there is a continued need for alternative methods to control dollar spot on turfgrass without undue phytotoxic effects and improved turf quality. It would be particularly useful if such methods and compositions utilized chlorothalonil in an amount at or below its annual maximum allowable application rate.

In accordance with the present invention, it has now been discovered that the effectiveness of chlorothalonil in the suppression or controlling of dollar spot on turfgrass is enhanced when it is applied at reduced rates in combination with a nonphytotoxic activity improving amount acibenzolar-S-methyl. The level of turfgrass quality also is greatly enhanced.

Accordingly, the present invention provides a method of suppressing or controlling dollar spot on turfgrass which comprises applying to the turfgrass, the locus thereof or the seeds thereof, a fungicidally effective non-phytotoxic amount of a combination of (A) chlorothalonil and (B) acibenzolar-s-methyl, wherein (A) is applied at a rate of from 2,000 to 10,000 g/ha and (B) is applied at a rate of from 4 to 20 g/ha.

In one embodiment, the method of the invention is employed under either pre-disease conditions or under low to moderate dollar spot disease pressure.

In another embodiment, the method of the invention is employed under conditions indicative of possible heavy disease pressure or under actual conditions of heavy disease pressure.

In accordance with the present invention, the method can be practiced with a single application that, optionally, is repeated in suitable intervals as necessary to suppress or control dollar spot disease in turfgrass. Advantageously, in the practice of the methods of the invention, the number of re-treatments or re-applications of the combination of (A) and (B), is greater than the number of re-treatments typically possible with chlorothalonil solo formulations due to the enhanced chlorothalonil (A) activity which allows application at reduced rates, which enhanced activity is occasioned by the combination with (B) when applied at a rate of from 4 to 20 g/ha per application.

In addition, the amount of (B) suitable for enhancing the activity of (A) not only is nonphytotoxic to the turfgrass, it also further improves the quality of the turfgrass to which it is applied. Accordingly, the method of the invention is useful both to (1) manage dollar spot disease by suppressing or controlling the dollar spot microorganisms and (2) enhance the quality of the turfgrass to which it is applied. The method of the invention enhances the ability of end-users such as lawn care operators, golf course technicians and the like to manage, suppress or control turfgrass dollar spot disease issues with chlorothalonil formulations without reaching chlorothalonil application rate limits.

The method according to the invention also is suitable to improve the quality of turfgrass. Therefore, in another aspect of the present invention, a method to improve the quality of turfgrass is provided, which comprises applying to the turfgrass, the locus thereof or seeds thereof a turf quality enhancing, non-phytotoxic amount of a combination of (A) chlorothalonil and (B) acibenzolar-s-methyl.

As noted above, in one embodiment, in the practice of the methods of the invention, chlorothalonil (A) is applied at a rate of from 2,000 to 10,000 g/ha and acibenzolar-S-methyl (B) is applied at a rate of from 4 to 20 g/ha.

In one embodiment, the method of suppressing or controlling dollar spot and the method to improve the quality of turfgrass comprises application to the turfgrass, the locus thereof or seeds thereof of a combination of (A) and (B) in a weight ratio of from 300:1 to 600:1.

In another embodiment, the method of suppressing or controlling dollar spot comprises application to the turfgrass, the locus thereof or seeds thereof of a fungicidally effective non-phytotoxic amount of a combination of (A) and (B) either pre-disease, or under low to moderate dollar spot disease pressure.

In another embodiment, the method of suppressing or controlling dollar spot, or the method to improve the quality of turfgrass comprises a treatment regime, where the combination of (A) and (B) at the foregoing rates and ratios is re-applied to the turfgrass or to the locus thereof at intervals of from 5 to 25 days, up to the cumulative maximum labeled rate for chlorothalonil per turf growing season for the specific turfgrass locus being treated according to existing restrictions. For example, in one embodiment, chlorothalonil is applied up to a cumulative maximum application rate of 100 kg/ha per turf growing season.

In a more specific embodiment, in the practice of the methods of the invention, the combination of (A) and (B) is re-applied to the turfgrass or the locus thereof at intervals of from 7 to 21 days; more specifically, from 7 to 14 days, up to the cumulative maximum labeled rate for chlorothalonil for the turfgrass locus being treated.

Specific turfgrass loci suitable for the methods of the invention include those listed on the current product label for Daconil Action™ which is incorporated by reference herein. For example, suitable turfgrasses include sod farms; turf on golf courses such as roughs, fairways, tees and greens; professional and collegiate athletic fields; and lawns around commercial and industrial buildings.

In another aspect of the methods of the invention, one or both of (A) and (B) can be applied to the turfgrass or the locus thereof using turfgrass seed as a carrier.

In a further aspect, the method of suppressing or controlling dollar spot comprises applying to the turfgrass, the locus thereof or seeds thereof a fungicidally effective non-phytotoxic amount of a composition comprising a mixture of (A) chlorothalonil and (B) acibenzolar-s-methyl.

In a further aspect, the method to improve the quality of turfgrass comprises applying to the turfgrass, the locus thereof or seeds thereof a turf quality enhancing non-phytotoxic amount of a composition comprising a mixture of (A) chlorothalonil and (B) acibenzolar-s-methyl.

Compositions comprising mixtures of (A) and (B) used in the methods of the present invention can be tank mixtures or premixes wherein the composition may further comprise adjuvants, solvents, carriers, surfactants or extenders.

As used herein the phrase "quality" of turfgrass is meant to include visual quality of turfgrass and functional quality of turfgrass.

"Visual quality" of turfgrass relates to the visual appearance, such as density (the number of aerial shoots per unit area), uniformity (for example uniformity of texture, e.g. width of the leaf blades, which can be fine-textured as for example in red fescue or coarse-textured as for example in tall fescue), colour or smoothness (which affects for example the playability of a golf course).

"Functional quality" of turfgrass relates to, for example, rigidity (resistance of the turfgrass leaves to compression and is related to the wear resistance of a turf), elasticity (tendency of the turfgrass leaves to spring back once a compressing force is removed), resiliency (capacity of a turf to absorb a shock without altering its surface characteristics), ball roll (average distance a ball travels upon being released to a turf surface), yield (measure of clippings removed with mowing), verdure (measure of amount of aerial shoots remaining after mowing), rooting (amount of root growth evident at any one time during the growing season) and recuperative capacity (capacity of turfgrasses to recover from damage caused by disease organism, insects, traffic and the like).

An improvement in the quality of turfgrass can relate to one of the mentioned visual or functional quality characteristics or to any combination of these quality characteristics.

According to the present invention, an "improvement" is a measurable or noticeable increase in a given turfgrass quality characteristic over the same turfgrass quality characteristic produced under the same conditions, but without the application of the subject method.

An improvement in the quality characteristics of turfgrass is, for example, a greener or more pleasant, leaf colour of the turf.

According to the invention, by "turfgrass" there is understood an annual or perennial Gramineae. Said gramineae preferably belongs to one or more of the genera *Agropyron, Agrostis, Axonopus, Bromus, Buchloë, Cynodon, Eremochloa, Festuca, Lolium, Paspulum, Pennisetum, Phleum, Poa, Stenotaphrum* or *Zoysia*. More preferably, said gramineae belongs to one or more of the genera *Agrostis,*

*Buchloë, Cynodon, Eremochloa, Festuca, Lolium, Paspulum, Pennisetum, Poa, Stenotaphrum* or *Zoysia*.

According to the invention by "turf" is understood as a group of turfgrass, which covers a surface area of ground and is subject to regular maintenance.

The present invention can be practiced with all turfgrasses, including cool season turfgrass and warm season turfgrass.

Examples of cool season turfgrasses are: Bluegrasses (*Poa* L.), such as Kentucky Bluegrass (*Poa pratensis* L.), Rough Bluegrass (*Poa trivialis* L.), Canada Bluegrass (*Poa compressa* L.) and Annual Bluegrass (*Poa annua* L.); Bentgrasses (*Agrostis* L.), such as Creeping Bentgrass (*Agrostis palustris* Huds.), Colonial Bentgrass (*Agrostis tenius* Sibth.), Velvet Bentgrass (*Agrostis canina* L.) and Redtop (*Agrostis alba* L.); Fescues (*Festuca* L.), such as Creeping Red Fescue (*Festuca rubra* L.), Chewings Fescue (*Festuca rubra* var. *commutata* Gaud.), Sheep Fescue (*Festuca ovina* L.), Hard Fescue (*Festuca longifolia*), Tall Fescue (*Festuca arundinacea* Schreb.), Meadow Fescue (*Festuca elatior* L.); Ryegrasses (*Lolium* L.), such as Perennial Ryegrass (*Lolium perenne* L.), Annual (Italian) Ryegrass (*Lolium multiflorum* Lam.); Wheatgrasses (*Agropyron* Gaertn.), such as Fairway Wheatgrass (*Agropyron cristatum* (L.) Gaertn.), Western Wheatgrass (*Agropyron smithii* Rydb.). Other cool season turfgrasses include Smooth Brome (*Bromus inermis* Leyss.) and Timothy (*Phleum* L.).

Examples of warm season turfgrasses are Bermudagrasses (*Cynodon* L. C. Rich), Zoysiagrasses (*Zoysia* Willd.), St. Augustinegrass (*Stenotaphrum secundatum* (Walt.) Kuntze), Centipedegrass (*Eremochloa ophiuroides* (Munro.) Hack.), Carpetgrass (*Axonopus* Beauv.), Bahiagrass (*Paspalum notatum* Flugge.), Kikuyugrass (*Pennisetum clandestinum* Hochst. ex Chiov.), Buffalograss (*Buchloe dactyloides* (Nutt.) Engelm.) and Seashore *paspalum* (*Paspalum vaginatum* swartz).

The method according to the present invention is effective to suppress or control turfgrass against incidence of dollar spot.

The method according to the invention is particularly effective to suppress or control turfgrass against developing dollar spot occasioned by *Sclerotinia homeocarpa, Lanzia* or *Moillerodiscus* spp. either pre-disease or under low to moderate disease pressure, such as when conditions are becoming favorable for disease or disease has just been detected.

In one embodiment, low disease pressure indicates a level of disease of from 0 to 10%; and moderate disease pressure indicates a level of disease of from 10 to 20% incidence of dollar spot disease (for example, a percentage calculated based on the number of dollar spot infection centers per unit area of the turfgrass being treated). In another embodiment, pre-disease or low to moderate disease pressure means that environmental conditions are not ideal for a full blown epidemic leading to heavy disease pressure.

In another embodiment, heavy disease pressure means that environmental conditions are ideal for a full blown epidemic leading to heavy disease pressure in check plots (21-100%). The methods of the invention are suitable to suppress or control disease under such conditions prior to disease development or when disease has just been detected.

The method according to the invention is particularly effective to suppress or control turfgrass against *Sclerotinia homeocarpa*.

The method according to the invention is particularly effective to suppress or control turfgrass against *Lanzia* spp.

The method according to the invention is particularly effective to suppress or control turfgrass against *Moillerodiscus* spp.

The term "locus" of turfgrass as used herein is intended to embrace the place on which the turfgrass are growing, the place where the seeds of the turfgrass are sown or the place where the seeds of the turfgrass will be placed for subsequent plant growth. According to the invention, the "locus" of a turf can relate to soil or to a substrate. An example for such a locus is a golf course, on which turfgrass is managed.

According to the invention the term "soil" means natural soil, which is typically present on a land area, such as soil being present on a golf course, or means soil, that has been modified, such as soil being granulated and/or treated with agrochemicals, such as for example fertilizers. An example of granulated and/or treated soil is disclosed in U.S. Pat. No. 5,265,372.

According to the invention the term "substrate" means a medium for the growth of turfgrass and the like, suited for application to a variety of existing ground structures. Typically, such mediums are soil-free mixtures that include sufficient proportions of ingredients of elastomeric granules, suitable binding emulsion, mineral aggregate, filler and controlled release plant nutrient particles, so that when laid and cured, said mixture produces a water permeable, resilient substrate having air pockets through which a root system of turfgrass can penetrate. Turfgrass growing on said substrate can form a turf, which can be applied to non-porous surfaces, such as for example roofs of buildings, terraces and other hard surface areas, or to porous surfaces, such as for example football fields or golf courses. Examples of such substrates are described in WO 2005/002323. Elastomeric granules can be, for example, granules of rubber, granules of recycled vehicle tyre rubber or mixtures thereof.

According to the invention the term "applied" means either simultaneously or sequentially. More specifically, in the practice of the method, the compounds (A) and (B) of the invention may be applied either simultaneously or sequentially. If administered sequentially, the components may be administered in any order in a suitable timescale, for example, with no longer than 24 hours between the time of administering the first component and the time of administering the last component. Suitably, all the components are administered within a timescale of a few hours, such as one hour. If the components are administered simultaneously, they may be administered separately or as a tank mix or as a pre-formulated mixture of all the components or as a pre-formulated mixture of some of the components tank mixed with the remaining components.

In accordance with the method of the present invention, the compounds (A) and (B) are applied to the turfgrass by treating the turfgrass, the locus thereof or seeds thereof.

Fungicidal compositions used in the method of the invention can be prepared on site by the end-user shortly before application to the turfgrass, the locus thereof or seeds thereof by mixing in aqueous solution a chlorothalonil containing composition, an acibenzolar-S-methyl containing composition and, optionally, a suitable surfactant or adjuvant. Such compositions are typically referred to as "tank-mix" compositions.

Alternatively, the compositions used in the method of the invention may be provided to the end-user already formulated, either at the desired dilution for application ("ready to use" compositions) or requiring dilution, dispersion, or dissolution in water by the end-user ("concentrate" compositions). Such preformulated concentrates can be liquids or particulate solids.

Water application volumes for applying the combination of (A)+(B) in accordance with the method range from 500 to 1000 liters per hectare.

The amount of compounds (A) and (B) to be applied in the practice of a method according to the invention will depend on various factors, such as the subject of the treatment, such as, plants, turfgrass locus or seeds; the type of treatment, such as, for example spraying, spreading or seed dressing; the purpose of the treatment, such as, for example suppression or control dollar spot; the type of dollar spot fungi to be controlled; enhancing turf quality, the application time; environmental conditions, the number of re-treatment intervals desired or the turfgrass species.

In one embodiment of the invention, the methods according to the invention are carried out by applying or treating the turfgrass, the locus thereof or the seeds thereof with a fungicidally effective non-phytotoxic amount of a composition comprising a mixture of (A) and (B) according to the invention.

In another embodiment of the invention, the methods according to the invention are carried out by applying or treating the turfgrass, the locus thereof or seeds thereof with a fungicidally effective non-phytotoxic amount of a combination of (A) and (B) according to the invention.

In yet another embodiment of the invention, the methods according to the invention are carried out by applying or treating the turfgrass, the locus thereof or seeds thereof with a turf quality enhancing non-phytotoxic amount of a combination comprising (A) and (B), either pre-disease or under low to moderate disease pressure, where the chlorothalonil (A) is applied at a rate of from 2,000 to 10,000 g/ha and acibenzolar-S-methyl (B) is applied at a rate of from 4 to 20 g/ha.

Application to Turfgrass:

The methods according to the invention can be practiced by treating the turfgrass with a combination comprising an effective amount of (A) and (B) according to the invention. Within said embodiment of the invention, the combination containing (A) and (B) is suitably applied to the turfgrass by spraying or spreading. Treatment of turfgrass in accordance with the methods of the invention may be performed by lawn care operators or golf course technicians.

In one embodiment of the inventive methods, to maintain high quality, healthy turfgrass on the intended surface area of ground, such as for example, a golf course, a sports field, a park area or a home lawn, and to protect said turfgrass against dollar spot diseases, combinations comprising (A) and (B) are applied to the turfgrass once or more than once during maintenance of the turfgrass.

Suitably, the methods of the invention are practiced by application of a combination comprising (A) and (B) once or more than once during a growing season of the turfgrass, in particular, at intervals of from 5 to 21 days, more particularly, at intervals of from 7 to 14 days, either pre-disease or under low to moderate dollar spot disease pressure. In one embodiment, the methods of the invention comprise from 6 to 8 applications of a combination of (A) and (B) at intervals of from 7 to 14 days.

Advantageously, in the practice of the method of suppressing or controlling dollar spot according to the invention it is possible to inhibit or destroy the dollar spot pathogens which occur on turfgrass, while at the same time the parts of turfgrass which grow later are also protected from attack by dollar spot pathogens.

In accordance with the method of the invention for dollar spot suppression or control, the combination of (A) and (B) is applied before disease or after low to moderate infection of the turfgrass by the fungi which cause dollar spot.

When applied to the turfgrass for suppression or control of dollar spot, chlorothalonil (A) is typically applied at a rate of from 2000 to 10,000 g/ha; from 3000 to 10000 g/ha; suitably from 3000 to 8000 g/ha, also suitably from 3000 to 5000 g/ha.

When applied to the turfgrass for enhancing suppression or control of dollar spot, acibenzolar-S-methyl (B) is typically applied at a rate of from 4 to 20 g/ha; from 5 to 16 g/ha (greens, for example); suitably from 5 to 12 g/ha (fairways, for example); also suitably from 7 to 10 g/ha (fairway, for example).

As noted, compositions used in the method of the invention comprise chlorothalonil and acibenzolar-S-methyl in an activity improving amount. In the compositions used in the method of this invention, the weight ratio of chlorothalonil to acibenzolar-S-methyl at which the fungicidal effect is improved lies within the range of between about 300:1 and about 600:1. Suitably, the weight ratio of chlorothalonil to acibenzolar-S-methyl is about 500:1

In another aspect, suppression or control of dollar spot is achieved by re-applying a fungicidally non-phytotoxic amount of the combination of (A):(B), suitably at the foregoing rates and weight ratios, at intervals of from 5 to 21 days, suitably from 7 to 14 days, during the turf growing season.

In a particular embodiment, 6 to 8 applications of a combination (A)+(B) is applied at 14 day intervals, pre-disease or under low to moderate disease pressure during the turf growing season.

Application to the Locus of the Turfgrass:

The compositions used in the method according to the invention can be applied to the turfgrass by treating the locus of the turfgrass with a composition comprising (A) and (B) according to the invention.

Application of compositions used in the method of the invention to a locus covers liquid (sprayable) or granular (active ingredient (a.i.) on inert and a.i. on fertilizer) (spreadable) applications as well.

For example, in the practice of method of the invention compositions comprising (A) and (B) can be applied to the soil before or after the seeds of the turfgrass are sown or placed into the soil; or such compositions are applied according to the method of invention to a substrate for the growth of turfgrass before or after the seeds of the turfgrass are placed into the substrate; or the compositions applied according to the method of the invention can be applied to the soil before turfgrass grown on a substrate are placed on top of the soil together with the substrate.

In one embodiment, according to the method of the invention compositions comprising (A) and (B) are applied to the turfgrass as a sprayable liquid formulation. In another embodiment, such compositions are applied to the turfgrass as a granular formulation. Suitable granules include inert and fertilizer granules. The active ingredient may be dispersed throughout, impregnated into, or coated on the surface of the granules.

Application to the Seeds of the Turfgrass:

The method according to the invention also can be practiced by applying the compositions containing (A) and (B) to the seeds of the turfgrass by treating the seeds with such a composition. When the method according to the invention involves using combinations of (A) and/or (B) for treating seed, rates of 0.001 to 50 g of the compound mixture per kg of seed, suitably from 0.01 to 10 g per kg of seed, are generally sufficient. In one embodiment, an amount of seed used as a carrier for (A) and/or (B) can be applied to the soil or substrate to deliver a suitable amount of the active ingredients.

The compositions used in the methods of the invention may be employed in any conventional form, for example in the form of a twin pack, a powder for dry seed treatment (DS), an emulsion for seed treatment (ES), a flowable concentrate for seed treatment (FS), a solution for seed treatment (LS), a water dispersible powder for seed treatment (WS), a capsule suspension for seed treatment (CF), a gel for seed treatment (GF), an emulsion concentrate (EC), a suspension concentrate (SC), a suspo-emulsion (SE), a capsule suspension (CS), a water dispersible granule (WG), an emulsifiable granule (EG), an emulsion, water in oil (EO), an emulsion, oil in water (EW), a micro-emulsion (ME), an oil dispersion (OD), an oil miscible flowable (OF), an oil miscible liquid (OL), a soluble concentrate (SL), an ultra-low volume suspension (SU), an ultra-low volume liquid (UL), a technical concentrate (TK), a dispersible concentrate (DC), a wettable powder (WP) or any technically feasible formulation in combination with agriculturally acceptable adjuvants.

Said compositions used according to the methods of invention may be produced in conventional manner, e.g. by mixing the compounds (A) and/or (B) with at least one appropriate formulation adjuvant.

The term "formulation adjuvant" according to the invention denotes a natural or synthetic, organic or inorganic material with which the compounds (A) and (B) are combined in order to facilitate its application to turf. This adjuvant is hence generally inert, and it must be agriculturally acceptable, in particular to turf.

The formulation adjuvant can be a carrier or a surfactant. In compositions according to the invention more than one adjuvant can be present, in such embodiments more than one carrier and/or more than one surfactant can be present, a non-limiting example would be one carrier and two surfactants.

The "carrier" can be a liquid carrier (water, alcohols, ketones, petroleum fractions, aromatic or paraffinic hydrocarbons, chlorinated hydrocarbons, liquefied gases, and the like) or a solid carrier.

Suitable liquid carriers are, but are not restricted to: aromatic hydrocarbons, in particular the fractions $C_8$ to $C_{12}$, such as xylene mixtures or substituted naphthalenes, phthalic esters such as dibutyl or dioctyl phthalate, dipropylene glycol dibenzoate, aliphatic hydrocarbons such as cyclohexane or paraffins, alcohols and glycols as well as their ethers, esters and diesters, such as ethylene glycol monomethyl ether, ketones such as cyclohexanone, strongly polar solvents such as, but not restricted to, N-methyl-2-pyrrolidone, dimethyl sulfoxide or dimethylformamide, and, if appropriate, epoxidized vegetable oils or soybean oil; or water.

Suitable solid carriers are, but are not restricted to: aluminium silicate, urea, sodium sulphate, talc, calcium sulphate or potassium sulphate and seed.

According to the invention a single carrier or a mixture of two or more carriers may be present in the composition(s) used in the methods according to the invention.

"Surfactants" are non-ionic, cationic, amphoteric and/or anionic surfactants having good emulsifying, dispersing and wetting properties. According to the invention a single surfactant or a mixture of two or more surfactants may be present. The surfactants customarily employed in formulation technology are described, inter alia, in the following publications: "McCutcheon's Detergents and Emulsifiers Annual", MC Publishing Corp., Glen Rock, N.J., 1988 and M. and J. Ash, "Encyclopedia of Surfactants", Vol. I-III, Chemical Publishing Co., New York, 1980-1981.

Among the surfactants there may be mentioned, e.g., polyacrylic acid salts, lignosulphonic acid salts, phenolsulphonic or (mono- or di-alkyl)naphthalenesulphonic acid salts, laurylsulfate salts, polycondensates of ethylene oxide with lignosulphonic acid salts, polycondensates of ethylene oxide with fatty alcohols or with fatty acids or with fatty amines, substituted phenols (in particular alkylphenols or arylphenols such as mono- and di-(polyoxyalkylene alkylphenol) phosphates, polyoxyalkylene alkylphenol carboxylates or polyoxyalkylene alkylphenol sulfates), salts of sulphosuccinic acid esters, taurine derivatives (in particular alkyltaurides), polycondensates of ethylene oxide with phosphated tristyrylphenols and polycondensates of ethylene oxide with phosphoric esters of alcohols or phenols.

A seed dressing formulation is applied in a manner known per se to the seeds employing the compositions according to the invention and a diluent in suitable seed dressing formulation form, e.g. as an aqueous suspension or in a dry powder form having good adherence to the seeds. Such seed dressing formulations are known in the art. Seed dressing formulations may contain the active ingredients in encapsulated form, e.g. as controlled release capsules or microcapsules.

The compositions used in the methods according to the invention may comprise one or more formulation additives, such as, but not limited to, biocides, anti-freeze, stickers, thickeners and compounds that provide adjuvancy effects including, for example, one or more phthalocyanines or copper phthalocyanines including pigment green such as pigment green 7; phthalocyanine green g; or pigment green 42.

In general, when phthalocyanines or copper phthalocyanines are present in compositions used in the methods according to the invention, the rate of application to the turfgrass or to the locus of the turfgrass is from 0.001 to 10 kilograms of phthalocyanine per hectare (kg/ha), suitably from about 0.01 to about 2 kg/ha, more suitably from about 0.1 to about 1 kg/ha, most suitably from about 0.2 to about 0.8 kg/ha.

The compositions used in the methods according to the invention may comprise one or more additional active ingredients, such as a fungicide, insecticide, herbicide or growth regulator. An example would be a composition that comprises another fungicide. Any suitable fungicide or herbicide may be used in the composition, for example to provide control of a broader spectrum of pests, to overcome problems and delay the onset of resistance, or to provide improved efficacy though an additive or synergistic effect of the active ingredients. Turf wetting agents may also be used in conjunction with the method of the invention. Suitable examples include Revolution® or Radiance® (Aquatrols); and Qualibra™ (Syngenta).

In one embodiment, the methods of the invention for suppressing or controlling dollar spot on turfgrass as specified herein contemplate one or more additional active ingredients being applied selected from the list comprising azoxystrobin; trinexapac-ethyl; paclobutrazole; neonicotinoids such as thiamethoxam and imidacloprid; bisamides such as cyantraniliprole and chlorantraniliprole; fluazinam; propiconazole, difenoconazole, cypraconazole; fludioxonil; mefenoxam; cyprodinil; thiophanate methyl; iprodione; triadimefon; propamocarb; fosetyl-al; flurprimidol; flutalonil; pyraclostrobin; boscalid; vinclozolin; trifloxystrobin; myclobutanil; fenarimol; SDHI fungicides such as isopyrazam and solatenol; fluoxastrobin; phophonic acid derivatives such as phosphonic acid, monopotassium salt; abamectin; cis-jasmone; abamectin iron chelate mixtures; and lambda cyhalothrin.

In another embodiment, the methods of the invention contemplate a fungicidally effective non-phytotoxic amount of a composition comprising a mixture of chlorothalonil and ASM as noted above along with fungicides having protectant modes of fungicidal action being applied to the turfgrass or to the locus of the turfgrass. Suitable fungicides with protectant modes of action include fluazinam and mancozeb.

The practice of the methods of the invention also contemplate application of a fungicidally effective non-phytotoxic amount of a composition comprising a mixture of chlorothalonil and ASM as noted above along with fungicides having post infection modes of fungicidal action to the turfgrass or to the locus of the turfgrass. Suitable fungicides with post-infection modes of action include Triazoles including propiconazole, difenoconazole, cyproconazole, triticonazole, metconazole, triadimefon and tebuconazole Strobilurins including azoxystrobin trifloxystrobin, fluoxastrobin and pyraclostrobin Fludioxonil Thiabendazole, SDHIs including—boscalid, fluopyram, isopyrazam, penthiopyrad, solatenol Phenylamide including metalaxyl and mefonoxam.

The practice of the methods of the invention further contemplate application of a fungicidally effective non-phytotoxic amount of a composition comprising a mixture of chlorothalonil and ASM as noted above along with plant growth regulators (PGR). Suitable plant growth regulators for use in the inventive method include azole PGR chemistry (such as uniconazole, and paclobutrazol), cyclohexane carboxylates (such as trinexapac-ethyl, and prohexadione-calcium), pyrimidinyl carbinols (such as flurprimidol, and ancymidol), quarternary ammoniums (such as chlormequat-chloride, and mepiquat-chloride), and sulphonyl-amino phenyl-acetamides (such as mefluidide). Plant growth regulators such as trinexapac-ethyl are suitable for use in the practice of the method of the invention to improve turf colour, quality, reduce clippings and improve rooting.

In general, the compositions according to the invention include from 0.01 to 90% by weight of compounds (A)+(B), from 0 to 20% surfactant and from 10 to 99.99% carrier.

Concentrated forms of compositions used in the methods according to the invention generally contain in between about 2 and 80%, preferably between about 5 and 70% by weight of (A)+(B). Application forms of formulation may for example contain from 0.01 to 20% by weight, preferably from 0.01 to 5% by weight of a compound of chlorothalonil. Whereas commercial products will preferably be formulated as concentrates, the end user will normally employ diluted formulations.

The compounds (A) chlorothalonil and (B) acibenzolar-s-methyl are commercially available.

In a one embodiment of the present invention, compositions suitable for use in the methods according to the invention comprise 53.94% chlorothalonil, 0.11% acibenzolar-S-methyl and 45.95% inert ingredients, such as a composition sold under the designation Daconil Action™ (Syngenta)

The Examples which follow serve to illustrate the invention, "active ingredient" denoting a compounds (A)+(B)

FORMULATION EXAMPLE

| Suspension concentrate | |
|---|---|
| Active ingredients | 40% |
| Propylene glycol | 10% |
| Nonylphenol polyethylene glycol ether (15 mol of ethylene oxide) | 6% |
| Sodium lignosulfonate | 10% |
| Carboxymethylcellulose | 1% |
| Silicone oil (in the form of a 75% emulsion in water) | 1% |
| Water | 32% |

In preparing and SC, the finely ground active ingredients are mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

The following examples are for illustrative purposes only. The examples are not intended as necessarily representative of the overall testing performed and are not intended to limit the invention in any way.

BIOLOGICAL EXAMPLES

Enhanced control of turf dollar spot (*Sclerotinia homoeocarpa*) when acibenzolar-S-methyl is applied in combination with chlorothalonil is claimed. Control of turf dollar spot (*Sclerotinia homoeocarpa*) with reduced rates of acibenzolar-S-methyl plus chlorothalonil is also claimed.

Example 1. Disease Control

Daconil Action (54% chlorothalonil and 0.176% acibenzolar-S-methyl) and Quali-Pro Chlorothalonil 720 were applied at golf course fairway recommended rates of 2 fluid ounces per 1000 square feet of turf and reduced rates of 1.82, 1.59 and 1.3 fluid ounces per 1000 square feet of turf. These rates are equivalent to the following:

TABLE 1

| Treatment | Rate-fluid ounces/1000 sq. ft. | Chlorothalonil g ai/ha | acibenzolar-S-methyl g ai/ha |
|---|---|---|---|
| Daconil Action | 2.0 | 4600 | 9.2 |
| Daconil Action | 1.82 | 4160 | 8.3 |
| Daconil Action | 1.59 | 3640 | 7.3 |
| Daconil Action | 1.3 | 2980 | 6.0 |
| Quali-Pro Chlorothalonil 720 | 2.0 | 4600 | |
| Quali-Pro Chlorothalonil 720 | 1.82 | 4160 | |
| Quali-Pro Chlorothalonil 720 | 1.59 | 3640 | |
| Quali-Pro Chlorothalonil 720 | 1.3 | 2980 | |

Trials were conducted on creeping bentgrass (*Agrostis stolonifera*) and arranged in randomized complete block designs with four replications. Treatments were applied on a 14 day schedule. Typically 6 applications were applied per trial. Percent turf area exhibiting dollar spot symptoms were assessed throughout the trial period. Turf quality was also evaluated.

Dollar spot developed to significantly damaging levels at all locations. In Table 2, average number of dollar spot loci across ratings is provided within and across trials 1-5. In Table 3, percent dollar spot control is provided within and across trials 1-5. In Table 4, average number of dollar spot loci across ratings is provided within and across trials 6-8. In Table 5, percent dollar spot control is provided within and across trials 6-8.

All rates of Daconil Action (2.0, 1.82, 1.59, and 1.3 fluid ounces) were equal to or superior to the 2 oz rate of Quali-Pro Chlorothalonil 720. This includes the recommended label rate of 2.0 fluid ounces as well as reduced rates of 1.82, 1.59 and 1.3 fluid ounces. The 1.3 ounce rate of Daconil Action was numerically equal to the 2.0 and 1.82 fluid ounce rate of Quali-Pro Chlorothalonil 720 and significantly (P=0.10) superior to the 1.59 and 1.3 fluid ounce rates.

These data support the claim that Daconil Action (acibenzolar-S-methyl plus chlorothalonil) provides enhanced control of turf dollar spot (*Sclerotinia homoeocarpa*) over chlorothalonil applied alone. Applying acibenzolar-S-methyl in combination with chlorothalonil may allow for as much as a 30% rate reduction without loss of disease control.

Daconil Action is a unique blend of a multiple-site contact fungicide (chlorothalonil) with acibenzolar-S-methyl a systemic compound used for control of disease through induction of host plant resistance. The mode of action of acibenzolar-S-methyl mimics the natural systemic activated resistance (SAR) response found in most plant species. This SAR response does not involve direct activity against the target pathogens but relies on the plants natural defense mechanism.

TABLE 2

Average counts of dollar spot loci across all ratings dates within and across all trials 1-5.

| | | Total Dollar Spot Counts | | | | | |
|---|---|---|---|---|---|---|---|
| | oz/1000 sq. ft. | Trial 1 PA* | Trial 2 CT* | Trial 3 MI* | Trial 4 WI* | Trial 5 NJ* | AVG** |
| 1 Untreated Check | | 124.1 | 114.3 | 235.3 | 220 | 476.4 | 234.0 |
| 2 Daconil Action | 2.0 | 14.88 | 40.6 | 31 | 106.7 | 64.9 | 51.6 |
| 3 Daconil Action | 1.82 | 22.53 | 34.9 | 36.2 | 83.6 | 61.9 | 47.8 |
| 4 Daconil Action | 1.59 | 6.8 | 47.6 | 58.5 | 110.2 | 101.4 | 64.9 |
| 5 Daconil Action | 1.3 | 23.3 | 52.6 | 91.3 | 124.2 | 112.6 | 80.8 |
| 6 Quali-Pro Chlorothalonil | 2.0 | 36.7 | 50.2 | 74.9 | 121.1 | 106 | 77.8 |
| 7 Quali-Pro Chlorothalonil | 1.82 | 15.9 | 104.8 | 76.2 | 122.4 | 122.1 | 88.3 |
| 8 Quali-Pro Chlorothalonil | 1.59 | 58.7 | 41.6 | 131.9 | 195.4 | 124.5 | 110.4 |
| 9 Quali-Pro Chlorothalonil | 1.3 | 33.68 | 86.6 | 129.5 | 260.7 | 145.6 | 131.2 |

*Average number of dollar spot loci or infections across all rating dates within trials.
**Average number of dollar spot loci or infections across all rating dates and locations.

TABLE 3

Percent dollar spot control across all ratings within and across all trials 1-5.

| | | % Control | | | | | |
|---|---|---|---|---|---|---|---|
| Treatment | oz/1000 sq. ft. | Trial 1 PA* | Trial 2 CT* | Trial 3 MI* | Trial 4 WI* | Trial 5 NJ* | AVG** |
| 1 Untreated Check | | 0 | 0 | 0 | 0 | 0 | 0.0 |
| 2 Daconil Action | 2.0 | 88 | 64 | 87 | 52 | 86 | 75.4 abc*** |
| 3 Daconil Action | 1.82 | 82 | 69 | 85 | 62 | 87 | 77.0ab |
| 4 Daconil Action | 1.59 | 95 | 58 | 75 | 50 | 79 | 71.3a-d |
| 5 Daconil Action | 1.3 | 81 | 54 | 61 | 44 | 76 | 63.3de |
| 6 Quali-Pro Chlorothalonil | 2.0 | 70 | 56 | 68 | 45 | 78 | 63.5cde |
| 7 Quali-Pro Chlorothalonil | 1.82 | 87 | 8 | 68 | 44 | 74 | 56.4ef |
| 8 Quali-Pro Chlorothalonil | 1.59 | 53 | 64 | 44 | 11 | 74 | 49.1fg |
| 9 Quali-Pro Chlorothalonil | 1.3 | 73 | 24 | 45 | −19 | 69 | 38.6g |

*Average percent control of dollar spot across all rating dates within trials.
**Average percent control dollar spot across all rating dates and locations.
***Means with same letter not different, LSD (P = 0.10)

TABLE 4

Average counts of dollar spot loci across all ratings dates within and across all trials 6-8.

| | | Total Dollar Spot Counts | | | |
|---|---|---|---|---|---|
| | oz/1000 sq. ft. | Trial 6 IN* | Trial 7 CT* | Trial 8 WI* | AVG* |
| 1 Untreated Check | | 9.95 | 115.67 | 32.03 | 52.6 |
| 2 Daconil Action | 2.0 | 1.49 | 11.66 | 19.81 | 11.0 |
| 3 Daconil Action | 1.82 | 1.26 | 9.4 | 17.01 | 9.2 |
| 4 Daconil Action | 1.59 | 1.72 | 15.69 | 15.85 | 11.1 |
| 5 Daconil Action | 1.3 | 2.10 | 31.81 | 20.58 | 18.2 |
| 6 Quali-Pro Chlorothalonil | 2.0 | 2.31 | 28.4 | 30.01 | 20.2 |
| 7 Quali-Pro Chlorothalonil | 1.82 | 1.79 | 20.95 | 16.65 | 13.1 |
| 8 Quali-Pro Chlorothalonil | 1.59 | 2.96 | 22.94 | 20.71 | 15.5 |
| 9 Quali-Pro Chlorothalonil | 1.3 | 2.25 | 44.29 | 19.34 | 22.0 |

*Average number of dollar spot loci or infections across all rating dates within trials.
**Average number of dollar spot loci or infections across all rating dates and locations.

TABLE 5

Percent dollar spot control across all ratings within and across all trials 6-8.

| | | % Control | | | |
|---|---|---|---|---|---|
| Treatment | oz/1000 sq. ft. | Trial 6 IN | Trial 7 CT | Trial 8 WI | AVG |
| 1 Untreated Check | | (9.95) | (115.67) | (32.03) | (52.6) |
| 2 Daconil Action | 2.0 | 85.0 | 89.9 | 38.15 | 79 |
| 3 Daconil Action | 1.82 | 87.3 | 91.87 | 46.89 | 82.5 |
| 4 Daconil Action | 1.59 | 82.7 | 86.4 | 50.15 | 78.9 |
| 5 Daconil Action | 1.3 | 78.89 | 72.49 | 35.74 | 65.39 |
| 6 Quali-Pro Chlorothalonil | 2.0 | 76.7 | 75.4 | 6.30 | 61.5 |
| 7 Quali-Pro Chlorothalonil | 1.82 | 82.0 | 81.8 | 48.01 | 75.0 |

TABLE 5-continued

Percent dollar spot control across all ratings within and across all trials 6-8.

| | | % Control | | | |
|---|---|---|---|---|---|
| Treatment | oz/ 1000 sq. ft. | Trial 6 IN | Trial 7 CT | Trial 8 WI | AVG |
| 8 Quali-Pro Chlorothalonil | 1.59 | 70.2 | 80.16 | 35.34 | 70.5 |
| 9 Quali-Pro Chlorothalonil | 1.3 | 77.3 | 61.7 | 39.61 | 58.1 |

*Average percent control of dollar spot across all rating dates within trials.
**Average percent control dollar spot across all rating dates and locations.

Example 2. Turf Quality

Enhanced control of dollar spot with acibenzolar-S-methyl plus chlorothalonil was also apparent in turf quality ratings (Tables 6-7-). The lowest rate of Daconil Action, 1.3 fluid ounces, was numerically equal to the 2.0, 1.82 and 1.58 fluid ounce rate of Quali-Pro Chlorothalonil 720 and significantly (P=0.10) superior to the 1.3 fluid ounce rate. Applying acibenzolar-S-methyl in combination with chlorothalonil may allow for as much as a 30% rate reduction. This rate reduction will result in equal disease control with no loss in turf quality.

TABLE 6

Turf Quality Rating (1-9 Scale, 9 best) Across All Ratings Within and Across All Trials 1-5.

| | | AVG Turf Quality/trial All ratings | | | | | |
|---|---|---|---|---|---|---|---|
| Treatment | Oz/ 1000 sq. ft. | Trial 1 PA* | Trial 2 CT* | Trial 3 MI* | Trial 4 WI* | Trial 5 NJ | AVG** |
| 1 Untreated Check | | 5.4 | 6.2 | 4.2 | 5.9 | 5.0 | 5.3 g |
| 2 Daconil Action | 2.0 | 7.7 | 7.5 | 6.4 | 6.4 | 6.7 | 6.9 ab |
| 3 Daconil Action | 1.82 | 7.2 | 7.7 | 6.3 | 6.5 | 6.8 | 6.9 abc |
| 4 Daconil Action | 1.59 | 7.8 | 7.3 | 6.0 | 6.5 | 6.4 | 6.8 bcd |
| 5 Daconil Action | 1.3 | 7.2 | 7.4 | 5.6 | 6.6 | 6.1 | 6.6 cde |
| 6 Quali-Pro Chlorothalonil | 2.0 | 7.1 | 7.2 | 6.0 | 6.5 | 6.3 | 6.6 b-e |
| 7 Quali-Pro Chlorothalonil | 1.82 | 7.4 | 6.7 | 5.7 | 6.5 | 6.1 | 6.5 def |
| 8 Quali-Pro Chlorothalonil | 1.59 | 6.8 | 7.7 | 5.2 | 6.4 | 6.2 | 6.5 ef |
| 9 Quali-Pro Chlorothalonil | 1.3 | 7.1 | 6.5 | 5.0 | 6.4 | 6.0 | 6.2 f |

*Average turf quality (1-9 scale) across all rating dates within trials.
**Average turf quality (1-9 scale) across all rating dates and locations.
***Means with same letter not different, LSD (P = 0.10)

TABLE 7

Turf Quality Rating (1-9 Scale, 9 best) Across All Ratings Within and Across All Trials 6-8.

| | | AVG Turf Quality/trial All ratings | | | |
|---|---|---|---|---|---|
| Treatment | Oz/ 1000 sq. ft. | Trial 6 IN* | Trial 7 CT* | Trial 8 WI* | AVG** |
| 1 Untreated Check | | 3.0 | 3.7 | 5.7 | 4.1e*** |
| 2 Daconil Action | 2.0 | 5.7 | 6.7 | 6.4 | 6.2 a |

TABLE 7-continued

Turf Quality Rating (1-9 Scale, 9 best) Across All Ratings Within and Across All Trials 6-8.

| | | AVG Turf Quality/trial All ratings | | | |
|---|---|---|---|---|---|
| Treatment | Oz/ 1000 sq. ft. | Trial 6 IN* | Trial 7 CT* | Trial 8 WI* | AVG** |
| 3 Daconil Action | 1.82 | 6.2 | 6.8 | 6.2 | 6.4 a |
| 4 Daconil Action | 1.59 | 5.7 | 5.8 | 6.3 | 6.0 ab |
| 5 Daconil Action | 1.3 | 5.1 | 5.5 | 6.1 | 5.6 bcd |
| 6 Quali-Pro Chlorothalonil | 2.0 | 5.4 | 5.7 | 5.6 | 5.6 bcd |
| 7 Quali-Pro Chlorothalonil | 1.82 | 5.1 | 6.0 | 6.3 | 5.8 bc |
| 8 Quali-Pro Chlorothalonil | 1.59 | 5.0 | 5.5 | 6.2 | 5.5 cd |
| 9 Quali-Pro Chlorothalonil | 1.3 | 4.8 | 5.0 | 6.1 | 5.3 d |

*Average turf quality (1-9 scale) across all rating dates within trials.
**Average turf quality (1-9 scale) across all rating dates and locations.
***Means with same letter not different, LSD (P = 0.10)

These data support the claim that Daconil Action (acibenzolar-S-methyl plus chlorothalonil) provides enhanced control of turf dollar spot (Sclerotinia homoeocarpa) over chlorothalonil applied alone. Applying acibenzolar-S-methyl in combination with chlorothalonil may allow for as much as a 30% rate reduction without loss of disease control or turf quality.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims. All publications cited herein are hereby incorporated by reference in their entirety for all purposes to the same extent as if each individual publication were specifically and individually indicated to be so incorporated by reference.

The invention claimed is:

1. A method for controlling or suppressing dollar spot in cool-season turfgrass, comprising applying to the cool-season turfgrass or to the locus of the cool-season turfgrass, a fungicidally effective non-phytotoxic amount of a combination comprising (A) chlorothalonil and (B) acibenzolar-S-methyl, wherein (A) is applied at a rate of from 2,000 to 10,000 g/ha and (B) is applied at a rate of from 4 to 20 g/ha, wherein the combination of (A) and (B) is applied pre-disease or under low to moderate dollar spot disease pressure present in the turfgrass.

2. The method of claim 1, wherein the weight ratio of chlorothalonil to acibenzolar-S-methyl is from 300:1 to 600:1.

3. The method of claim 1, wherein chlorothalonil and acibenzolar-S-methyl are applied simultaneously together, separately, or in succession.

4. The method of claim 1, wherein a fungicidally effective non-phytotoxic amount of a composition comprising a mixture of chlorothalonil and acibenzolar-S-methyl is applied to the turfgrass or to the locus of the turfgrass.

5. The method of claim 1, using a composition comprising a combination of (A) and (B).

6. The method of claim 5, wherein the composition of (A) and (B) further comprises adjuvants, solvents, carrier, surfactants or extenders.

7. The method according to claim 6, wherein the composition comprises from 0.01 to 90% by weight of the combination of (A) and (B), from 10 to 99.99% of a carrier and from 0 to 20% of a surfactant.

8. The method of claim 1, wherein chlorothalonil is applied at the rate of from 3000 to 10000 g/ha.

9. The method of claim 1, wherein acibenzolar-S-methyl is applied at the rate of from 5 to 16 g/ha.

10. The method of claim 1, wherein the combined amount of chlorothalonil and acibenzolar-S-methyl that is applied to the turfgrass or to the locus thereof is between about 3000 to 5000 g/ha.

11. The method according to claim 1, wherein the phytopathogenic disease is caused by one or more phytopathogenic fungi selected from the group consisting of *Sclerotinia homeocarpa, Lanzia* or *Moillerodiscus* spp.

12. The method according to claim 1, wherein the turfgrass is an annual or perennial Gramineae belonging to at least one of the genera *Agropyron, Agrostis, Axonopus, Bromus, Buchloë, Cynodon, Eremochloa, Festuca, Lolium, Paspulum, Pennisetum, Phleum, Poa, Stenotaphrum* or *Zoysia*.

\* \* \* \* \*